United States Patent [19]

Hodgkin et al.

[11] Patent Number: 5,709,947
[45] Date of Patent: Jan. 20, 1998

[54] EPOXY RESINS BASED ON DIAMINOBISIMIDE COMPOUNDS

[75] Inventors: Jonathan Howard Hodgkin, Burwood; Mervyn Benjamin Jackson, Glen Waverley; John West Loder, South Yarra, all of Australia

[73] Assignee: Commonwealth Scientific and Industrial Research Organisation, Campbell, Australia

[21] Appl. No.: 460,388

[22] Filed: Jun. 2, 1995

Related U.S. Application Data

[62] Division of Ser. No. 30,302, Jan. 3, 1993, abandoned.

[30] Foreign Application Priority Data

Oct. 3, 1990 [AU] Australia ............ PK 2607/90

[51] Int. Cl.$^6$ ............ C08G 59/44; C08G 59/54
[52] U.S. Cl. ............ 428/413; 525/423; 525/504; 528/99; 528/109; 528/113; 528/117; 528/322; 548/429; 548/433; 548/461; 548/472; 548/473; 548/476; 548/513
[58] Field of Search ............ 525/423, 504; 528/99, 109, 113, 117, 322; 428/413; 548/433, 429, 461, 513, 472, 476, 473

[56] References Cited

U.S. PATENT DOCUMENTS

| | | | |
|---|---|---|---|
| 4,340,715 | 7/1982 | Gounder et al. | 528/99 |
| 4,622,383 | 11/1986 | Araps et al. | 528/345 |
| 4,705,833 | 11/1987 | Saito et al. | 525/504 |

*Primary Examiner*—Frederick Krass
*Attorney, Agent, or Firm*—Bacon & Thomas

[57] ABSTRACT

A method for the preparation of a diaminobisimide compound of the formula (I) substantially free of oligomers:

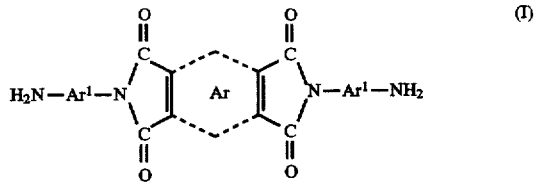

wherein $Ar^1$ is an optionally substituted aromatic residue which provides for good conjugation between the nitrogen containing groups; and Ar is an optionally substituted aromatic residue characterized in that at least two molar proportions of an aromatic diamine of the formula (II)

$$H_2N-Ar^1-NH_2 \qquad (II)$$

wherein $Ar^1$ is as defined above, are heated with one molar proportion of an aromatic tetracarboxylic acid of the formula (III) or the corresponding dianhydride, $$(HOOC)_2Ar(COOH)_2 \qquad (III)$$

wherein Ar is as defined above, optionally in the presence of a polar solvent and optionally including 0.1 to 2 molar proportions of a tertiary amine.

The compounds of formula (I) are useful curing agents in epoxy resin formulations.

17 Claims, No Drawings

EPOXY RESINS BASED ON DIAMINOBISIMIDE COMPOUNDS

This application is a division of application Ser. No. 08/030,302, filed Jan. 3, 1993, now abandoned.

This invention relates to diaminobisimide compounds suitable for use as curing agents in epoxy resins and to polymer matrices with high glass transition temperatures produced from the cured resins.

The so-called "epoxy resins" are a well known class of thermosetting resins which are prepared by reacting polyepoxides with a curing agent. A large variety of polyepoxides and curing agents are known and have been described in the literature. Epoxy resins are the most widely used resins in the production of advanced composites in which reinforcing fibres, especially carbon fibres, are coated with a formulation comprising a polyepoxide and a curing agent followed by curing to form a composite material. The preferred curing agents for such systems are aromatic diamines. Many of the cheaper aromatic diamines such as p-phenylene diamine, m-phenylene diamine, 4,4'-diaminodiphenylether, 4,4'-diaminophenylmethane and 4,4'-diaminodiphenylsulphone (DDS) are either oxidatively unstable or cause health and safety problems. The instability problems are generally caused by the conjugation between the two aromatic amino groups and commercial considerations have made it necessary to use less conjugated but high melting materials such as DDS.

A major problem in the advanced materials industry is that the use of epoxy resin formulations as either adhesives or composites involves hand fabrication and requires long and involved procedures to cure. The current toxicity and stability problems of available aliamines, such as m-phenylene diamine and diaminodiphenylmethane result in the use of insoluble, expensive and less processable diamines, such as DDS.

In attempts to improve the stability, decrease toxicity and improve the physical properties of these diamines, considerable research has recently gone into the; synthesis of many high molecular weight aliamines which are less conjugated, such as, for example, Shell Epon HPT 1062, shown below. This has been especially common in the area of epoxy resin hardeners (D. A. Scola, Advances in *Epoxy Resins*, 4, 165 (1984)) and in polyimides (T. Takeoshi, *Advances in Polymer Science* 94, 1 (1990)). Unfortunately, the methods of preparing these materials generally involve multistep reactions from costly starting materials or require thermally unstable quaternary carbon compounds or other chemically unsatisfactory atoms in the main chain.

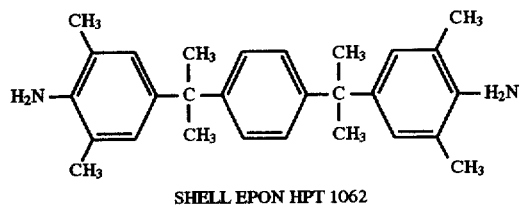

SHELL EPON HPT 1062

Recently, the synthesis of compounds with bisimide groups between reactive aromatic aliamines has been reported, such as in J. H. Hodgkin, *J Polymer Science:Polymer Chem Ed* 14, 409 (1976). As the imide group is common in very thermally stable polymers, these diaminobisimides have the potential to be useful aliamine monomers. However, apart from those made by D. A. Scola they are primarily high melting, insoluble materials. Scola's compounds have been tested as hardeners for epoxy resins. They were prepared by reacting aromatic diamines with a fluoroalkylidene aryl dianhydride to give the complex mixture of oligomeric compounds shown in Reaction Scheme 1 below. The complexity of the mixture is acknowledged by these research workers as resulting from multiple reactions of the starting aromatic diamines. As a consequence of this oligomer formation, the fluoroalkylidene aryl dianhydride shown in Reaction Scheme 1 is the only compound which can provide soluble and useful mixtures of hardener materials.

Reaction Scheme 1

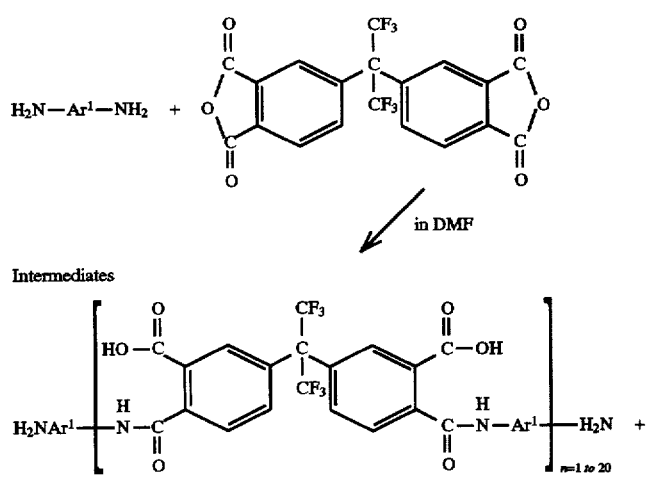

Intermediates

-continued
Reaction Scheme 1

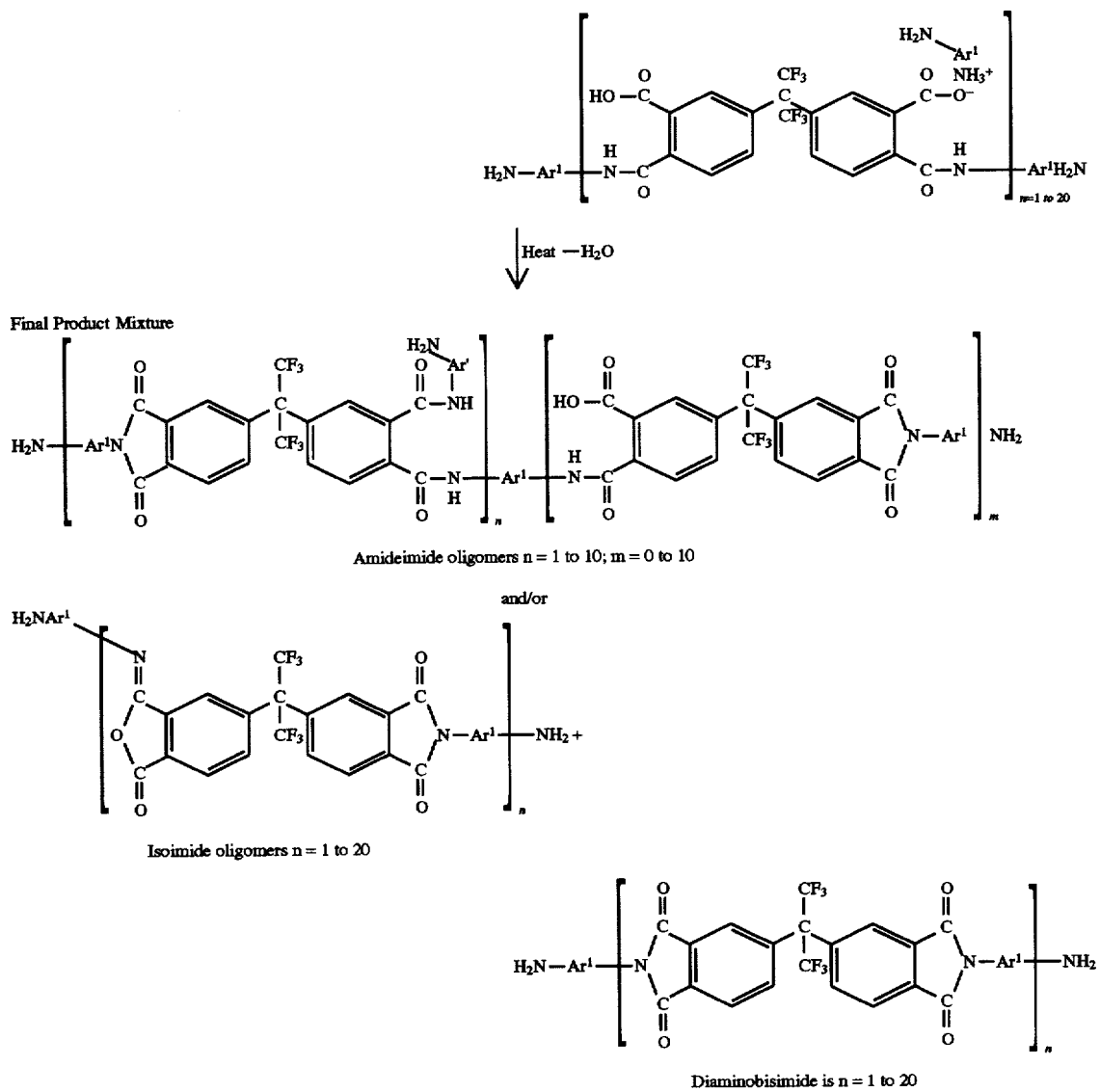

Amideimide oligomers n = 1 to 10; m = 0 to 10 and/or

Isoimide oligomers n = 1 to 20

Diaminobisimide is n = 1 to 20

Since purification of such mixtures is extremely difficult, they are used while contaminated with the oligomeric compounds and consequently produce cured resins with properties inferior to those expected if the pure diamine was used. Thus, the synthesis of diaminobisimide compounds of the formula (I) as shown below would be of great commercial utility.

We have now found that diaminobisimide compounds of the formula (I) can be prepared in one step and substantially free from oligomers and amide impurities by the use of carefully controlled reaction conditions.

The standard method of synthesizing polyimides used in the plastic industry involves reacting one mole of a pure diamine with one mole of a purified dianhydride in dry and highly purified polar solvents such as dimethylformamide, dimethylacetamide or N-methylpyrrolidone at room temperature and then heating the resulting polyamidoacids to above 180° C. to complete the cyclization.

The most successful previous method for synthesizing diaminobisimides is that described by N. K. Dorogova, et al, in which one mole of dianhydride (PMDA or BTDA) in dry dimethylformamide was added slowly to two moles of the diamine in the same solvent at 130° C. The optimum yield obtained was 70% for m-phenylenediamine.

The present invention provides a new method for preparing diaminobisimide compounds of the formula (I) substantially free of oligomers. The products of this method have improved stability and processing properties.

According to one aspect of the invention there is provided a method for the preparation of a diaminobisimide compound of the formula (I) substantially free of oligomers:

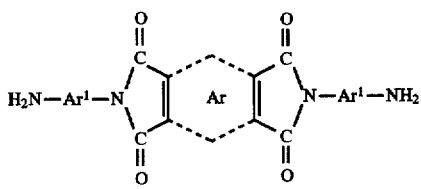

(I)

wherein

Ar¹ is an optionally substituted aromatic residue which provides for good conjugation between the nitrogen-containing groups; and Ar is an optionally substituted aromatic residue, characterized in that at least two molar proportions of an aromatic diamine the formula (II)

(II)

wherein Ar¹ is as defined above are heated with one molar proportion of an aromatic tetracarboxylic acid of the formula (III), or the corresponding dianhydride,

(III)

wherein Ar is as defined above, optionally in the presence of a polar solvent and optionally including 0.1 to 2 molar proportions of a tertiary mine.

As used herein the term "good conjugation" means that during imide formation from the diamine of formula (II), substitution of an electron-withdrawing group onto one of the nitrogen atoms suppresses the reactivity of the other nitrogen atom during the reaction.

Suitable Ar groups are aryl, bridged or bonded di- or poly-aryl, and heteroaryl. The Ar groups may be substituted with one or more alkyl, alkoxy, alkylthio, aryl, heteroaryl, aryloxy, alkylthio, dialkylamino, nitro, cyano or halo groups. One of the ordinary skill in the art understands that the substituents of the Ar group must be selected so that they do not participate in the imide formation reaction.

"Aryl" means an aromatic carbocyclic group, such as phenyl, naphthyl, and the like.

"Bridged or bonded di- or poly- aryl" means a group consisting of two or more aromatic carbocyclic ring systems, such as phenyl, naphthyl or the like joined by a bond, such as in biphenyl, or a bridging group, such as in sulphonyldiphenyl.

"Bridging group" includes for example $CF_3$—C—$CF_3$, $SO_2$, CO and O such as in compounds of the formula (IVa)

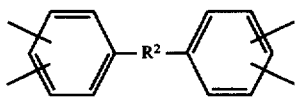

(IVa)

wherein $R^2$ is a divalent radical such as $CF_3$—C—$CF_3$, $SO_2$, $CH_2CO$ and O.

Generally the group Ar¹ may be selected from the groups listed above for Ar. However, because of the constraints imposed by the requirement of "good conjugation" (as defined above) some bridged di- or poly- aryl groups may not be suitable.

Thus for Ar¹, the bridging group (if present) must provide good conjugation between the amino groups of the diamine (II).

For example for groups of the formula (IVb) wherein $R^1$ is $CH_2$ or where the diamine is 3,3'-sulphonyldianiline, there is insufficient conjugation and oligomeric diaminoimides are formed. In contrast, benzidine and 4,4'-sulphonyldianilines have sufficient conjugation and give the desired diaminobisimide compound.

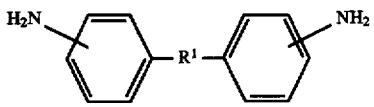

(IVb)

"Heteroaryl" means aromatic monocyclic or polycyclic groups containing at least one hetero atom such as nitrogen, oxygen or sulfur.

Examples of suitable "heteroaryl" groups are:

3- to 8-membered, more preferably 5- or 6-membered, heteromonocyclic groups containing 1 to 4-nitrogen atom (s), for example, pyrrolyl, imidazolyl, pyrazolyl, pyridyl, pyrimidyl, pyrazinyl, pyridazinyl, triazinyl;

condensed heterocyclic groups containing 1 to 5 nitrogen atom(s), for example, indolyl, isoindolyl, indolizinyl, benzimidazolyl, quinolyl, isoquinolyl, indazolyl, benzotriazolyl, etc.;

3 to 8-membered heteromonocyclic groups containing 1 or 2 sulfur atom(s) and 1 to 3 nitrogen atom(s), for example, thiazolyl, isothiazolyl, thiadiazolyl, etc.;

3 to 8-membered heteromonocyclic groups containing 1 or 2 sulfur atom(s), for example thienyl, etc.;

condensed heterocyclic groups containing 1 or 2 sulfur atom(s) and 1 to 3 nitrogen atom(s), for example, benzothiazotyl, benzothiadiazolyl, etc.;

3 to 8-membered heteromonocyclic groups containing an oxygen atom, for example, furyl, etc.;

condensed heterocyclic groups containing 1 to 2 sulfur atom(s), for example, benzothienyl, etc.; and condensed heterocyclic groups containing 1 or 2 oxygen atom(s), for example, benzofuranyl, etc.

"Alkyl" groups may be straight chain or branched and contain 1–20 carbon atoms. Suitable alkyl groups are methyl, ethyl, propyl, iso-propyl, n-butyl, iso-butyl, tert-butyl, n-pentyl, iso-pentyl, neo-pentyl, n-octyl, iso-octyl, decyl, cetyl, stearyl, and the like. "Alkoxy" and "allkylthio" mean such groups in which the alkyl moiety is a branched or unbranched saturated hydrocarbon group containing from one to eight carbon atoms, such as methyl, ethyl, propyl, iso-propyl, n-butyl, iso-butyl, tert-butyl and the like.

"Alkanoyl" may be formyl, acetyl, propionyl, butyryl, valeryl, isovaleryl, pivaloyl, hexanoyl, and the like.

Preferably the aromatic diamine of the formula (II) is sterically hindered, such as in compounds of the formula (VI)

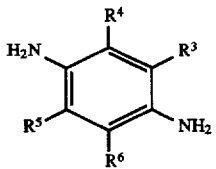

(VI)

wherein $R^3$, $R^4$, $R^5$ and $R^6$ are the same or different and each may be selected from alkyl, aryl, heteroaryl, nitro and halogen groups.

The present invention also provides a diaminobisimide compound of the formula (I) whenever prepared by the method defined above.

An important aspect of the method of the invention is the use of group conjugation which can be assisted by steric hindrance to achieve monosubstitution in aromatic aliamines where the two amino groups originally have similar reactivities. This type of monosubstitution is regularly used in many other areas of chemistry, for example in diisocyanate chemistry for polyurethane synthesis and in the Manrtich reaction synthesis of aminomethyl substituted pharmaceuticals (eg. Tramontini, *Synthesis* (1973) 703), but it is not well known in aromatic diamine synthetic reactions. It has not been possible previously to use these methods for diaminobisimide synthesis as the intermediate product of the reaction is a diaminodiacid of the Formula A as shown below and the free add groups react with the end amino groups to form oligomeric amides, amideimides, etc., as in Reaction Scheme 1.

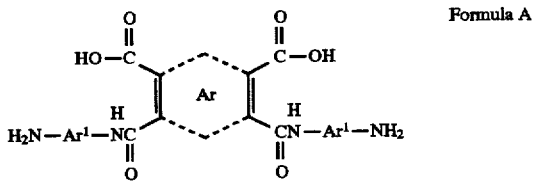

Formula A

It has been found that for less conjugated amines it is possible to use the endothermic reaction of an aromatic tetracarboxylic acid with the aromatic aliamine as shown in Reaction Scheme 2 to inhibit oligomer formation. It has been found that when one mole of the tetracarboxylic acid is mixed with two moles of the aliamine, due to ionic repulsion in aqueous solutions or even in relatively non-polar solvents such as acetone only one of the amino groups attaches to a carboxylic acid group (not the two ortho groups).

Formula B

In this reaction, the steric constraints of the adjacent peri carboxyl groups meant that the intermediate diaminodiacids either could not form or were so unstable that the acid groups could not react independently. This is not the case with other dianhydrides, especially the commercially important five membered ring anhydrides such as PMDA, BTDA or 6FDA.

PMDA

Reaction Scheme 2

The protonation of one of the amino groups in conjugated diamines depresses the protonation of the second amino group and hence prevents oligomeric salt formation (as seen by NMR and FTIR evidence and pKa measurements). When these salts are heated further (100°–250° C.) they cyclize directly to the monomeric diaminobisimides in high yields.

The use of group conjugation in synthesis of one particular series of diaminobisimides was reported by J. H. Hodgkin, *J Polymer Science:Polymer Chemistry* Ed Vol 14, 409 (1976) where the tetracarboxylic dianhydride used was 1,4,5,8-naphthalene tetracarboxylic dianhydride. The pure products of the reaction were of the Formula B -continued

BTDA

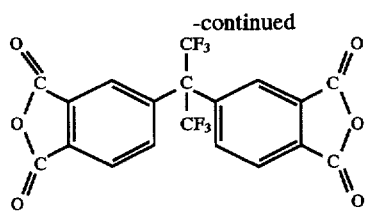

6 FDA

Where a dianhydride is used in the method of the invention it is preferred to add a strong base tertiary amine such as diaminobicyclooctane (DABCO) to the initial primary aromatic diamine solution in sufficient quantity to form a blocking salt with the free acid sites of the diamidodiacid until it is incorporated into the cyclized imide as shown in Reaction Scheme 3. The yield of the above reaction increased to 95% by this method.

solution or slurry under pressure which contrasts with most previous literature reports suggesting that imides are readily hydrolysed in water.

It has been further shown that in the case of aromatic diamines that are both conjugated and sterically hindered it is possible to form high yields of the diaminobisimide compounds of the formula (I) preferably by heating a molten mixture of the diamine and dianhydride together, provided the aliamine melts first and hence is always in much higher concentration in the reaction zone. Again steric hindrance, conjugation and a sufficiently high temperature is generally required to obtain cyclization of the intermediate diaminodiacid without formation of multiamido compounds or oligomers. Similar conditions may be used to form diaminobisimides from molten, sterically hindered, conjugated aromatic aliamines and aromatic tetracarboxylic acids. The reaction in this case is via the amine/acid salts as shown above in Reaction Scheme 2.

Reaction Scheme 3

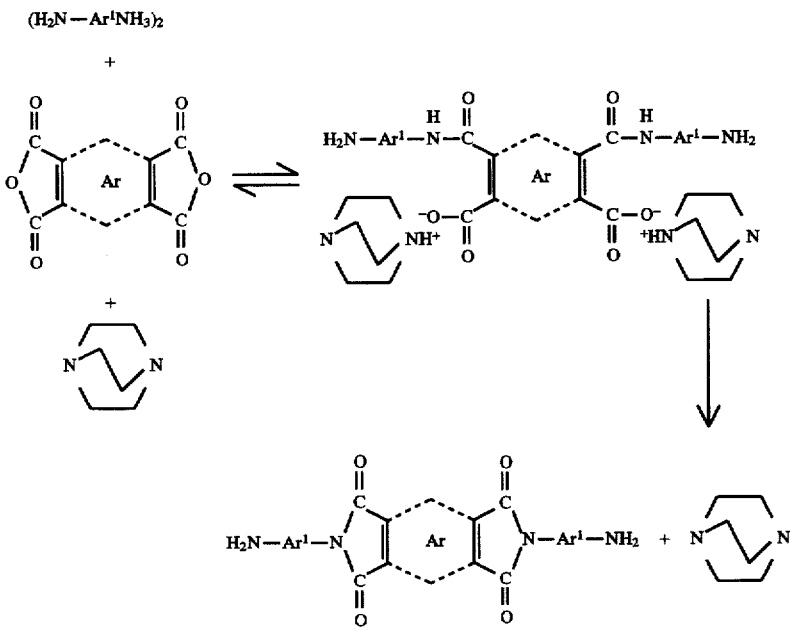

When the addition of the dianhydride is carried out at temperatures above the cyclization temperature of the amidoacids, preferably 120° to 200° C., relatively small amounts of the tertiary amine base are generally required.

As the reaction of an anhydride with a diamine is an exothermic reaction, this method only gives high yields of the pure diaminobisimide with strongly conjugated aliamines, that is only when the second amine loses considerable reactivity once the first amine has reacted. This has been found especially when steric hindrance, for example ortho aliphatic groups around the amines, is combined with conjugation to enhance the reactivity changes.

It has been found that when tetracarboxylic acids are used the diamine salts may be formed in a number of different solvents, such as, for example, acetone, wet dimethylformamide and dimethylacetamide. However, the use of water provides considerable advantages of cost reduction and ease of removal from the final product unlike the expensive and troublesome polar solvents which often complex with the final product.

The final cyclization may be carried out by heating preferably between 80° and 250° C., the dry salt or a water Sterically hindered amines can yield diaminobisimide compounds which are soluble in relatively non polar solvents, such as, for example, acetone, dichloromethane, chloroform and tetrahydrofuran. This may be contrasted with previously reported diaminobisimide compounds which are high melting insoluble materials except for those mixed oligomeric materials produced from the costly hexafluoroanhydride shown in Formula 1.

The diaminobisimide compounds of the present invention which are generally substantially free of oligomers are useful as thermally stable hardeners for advanced epoxy resin formulations and composites based on such formulations.

Thus, according to another aspect of the present invention there is provided a diaminobisimide compound of the formula (I) as defined above whenever prepared by the method of the invention for use as a curing agent (hardener) in an epoxy resin formulation.

According to a still further aspect of the present invention there is provided diaminobisimide compound of the formula (I) for use in the manufacture of high temperature resistant thermoplastic and thermoset polymeric materials.

Some of the diaminobisimide compounds of the formula (I) are novel and form a further aspect of the present invention.

Thus, according to a further aspect of the present invention there is provided a diaminobisimide compound of the formula (Ia)

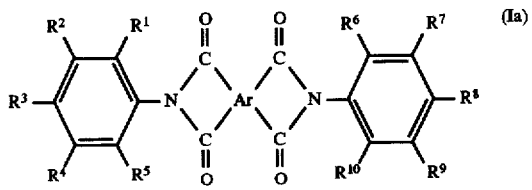

wherein $R^1$ to $R^{10}$ are the same or different and each may be selected from hydrogen, alkyl, thioalkyl, alkoxy, dialkylamino, alkylamino and amino; and Ar is as defined above;

with the proviso that at least one of $R^1$ to $R^5$ and $R^6$ to $R^{10}$ is an alkyl group and at least one of $R^2$ to $R^4$ and $R^7$ to $R^9$ is an amino group.

The diaminobisimide compound of the formula (I) is suitable for use as a curing agent (hardener) in an epoxy resin formulation.

The present invention further provides an epoxy resin formulation comprising a mixture of a curing agent and one or more polyepoxides, characterized in that the curing agent is a compound of the formula (I) as defined above.

Any suitable polyepoxides or mixtures thereof may be used in the resin formulations of the invention. The most readily available are N,N,N',N'-tetraglycidyl methylene dianiline (TGDDM) (e.g. Ciba Geigy MY720) and diglycidyl ethers of bisphenol A (DGEBA). For advanced composites, greater than 50 weight % of MY720 is preferred.

Particularly suitable polyepoxides are those prepared from "upper rim" calixarenes as described in our copending Australian Patent Applications Nos. PK 2610/90 and PK 3871/90.

The resin formulations of the invention may also contain various toughening polymers which may be either elastomers or thermoplastics and catalysts.

These resin formulations are easy to process and produce materials with improved properties such as higher Tg, toughness, toughenability and water resistance with less health hazards.

Still further according to the present invention there is provided an impregnated fibre reinforced material (prepregs), characterised in that the fibre reinforcements are coated with the epoxy resin formulation defined above.

In an additional aspect of the present invention there is provided an advanced composite material comprising an assembly of reinforcing fibres in a matrix of cured epoxy resin, characterized in that the cured epoxy resin is formed by heating the epoxy resin formulation as defined above.

Alkylated aromatic diaminobisimides of the formula (Ia) prepared from pyromellitic acid and Ethacure 100 (Formula Ib), referred to herein as CBH-103, and benzophenone tetracarboxylic acid and Ethacure 100 (Formula Ic), referred to herein as CBH-104 have been found to be easily made from these readily available starting materials and give cured epoxy resins and laminates with good properties. ("Ethacure" is a Registered Trade Mark).

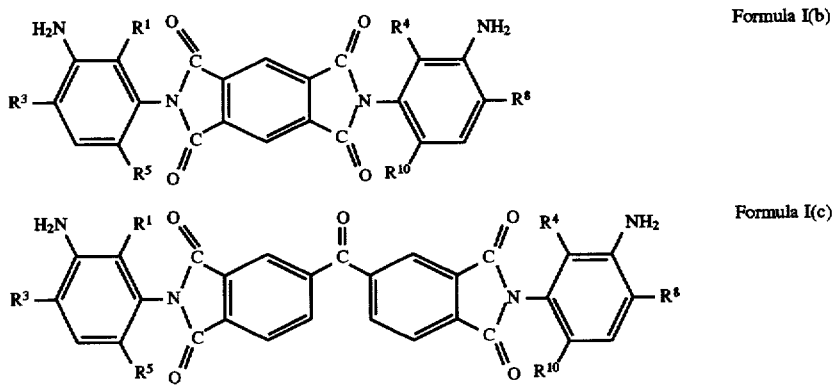

Formula I(b)

Formula I(c)

wherein any two of $R^1$, $R^3$ or $R^5$ are ethyl and the other is methyl and any two of $R^6$, $R^8$ and $R^{10}$ are ethyl and the other is methyl.

When at least three of the groups $R^1$, $R^5$, $R^6$, and $R^{10}$ in formula (Ia) are methyl or sterically larger groups the diaminobisimide compound is generally soluble in the solvents used commonly for prepregging, such as, for example, acetone and dichloromethane.

The relatively low melting point and good solubility of the compounds of formula (Ia) results in the preparation of the resins of the invention being simpler than conventional resins. For example, the epoxy resin of the invention comprising a compound of formula (Ia) as curing agent, together with polyepoxy resins such as DGEBA and TGDDM or mixtures thereof may be prepared by melt mixing using the following procedure:

1. Heating the epoxy resin formulation to a temperature sufficient to lower the viscosity to a level which enables the subsequent components to be incorporated satisfactorily in the mixer used.

2. Mixing in any toughening polymers and/or fillers required.

3. Incorporating the required quantity of diaminobisimide compound of formula (Ia).

4. Cooling the mixture as far as possible consistent with mixability before optionally adding a catalyst.

The epoxy resin formulations of the invention are generally liquids at processing temperatures in the range of 110° C. to 170° C. This is not possible with impure diaminobisimides as discussed in D. A. Scola, *Polymer Composites*, 4, 154 (1983). For example, when the compound of the formula (Ia) was derived from the reaction of Ethacure 100 (an amine wherein four of the R groups are ethyl, two are methyl and two are hydrogen) and pyromellitic acid. i.e. CBH-103, the composition could be easily poured at 150° C.

Alternatively, a solvent-containing formulation of lower viscosity may be prepared by dissolving the epoxy resin in solvent, for example, acetone and mixing it with a solution of the diaminobisimide compound of the formula (I) curing agent in the same solvent. Other components such as fillers, catalysts, or rubber modifiers may be added to the mixture if desired. The amount of solvent preferably used is the minimum consistent with the flow properties required for the subsequent use.

However, in the preparation of an epoxy resin formulation suitable for forming the prepregs as described below the amount of solvent is preferably increased to reduce the viscosity of the mix and a solution of rubber modifiers is added to provide tackiness.

The epoxy resin formulation may be applied to a reinforcing material such as a uni-directional tape made from reinforcing fibre or to a woven fibre cloth either from a formulated solution such as described above (preferably with a lower aliphatic ketone or halogenated hydrocarbon solvent) by brushing or dipping, or from a hot melt. Application may be manual or by a machine process including those involving transfer from a procoated transfer medium. In the case of solution coating, after air drying the prepreg is preferably flash dried to remove the last of the solvent (usually <100 ° C. for a short time) and stored at low temperature, preferably −10° C. or less.

To produce a cured resin matrix, the diaminobisimide compounds of the formula (I) may be mixed with polyepoxides known per se in the art or with experimental polyepoxides and cured at temperatures of preferably up to 250° C. The curing reaction may be catalysed by the addition of $BF_3^-$ ethylmine, $BF_3^-$ benzylamine or other known catalysts to the composition.

Composite materials may be prepared from a mixture of the epoxy resin and reinforcing material by subjecting the epoxy resin formulation, after forming into the desired shape and size to a heating cycle to cure the resin.

Resin impregnated fibre materials or prepregs may be laid down by any existing method for preparing composite materials including vacuum bagging on a caul plate or on an appropriate tool. Curing can be carried out in an autoclave, hot platten press or other device. A suitable curing cycle is programmed linear temperature increase from 20° C. to 180° C. followed by 4 h at 180° C.

Alternatively, the epoxy resin formulations may be used for Resin Transfer Moulding.

The invention is further illustrated by the following non-limiting examples.

EXAMPLE 2

Synthesis of 5,5'-carbonylbis[2-(4-aminophenyl)]-1H-isoindole-1,3(2H)-dione.

p- Phenylenediamine (2.16 g) and 1,4-diazabicyclo[2.2.2] octane (1.0 g) were dissolved in dimethylformamide (DMF) (50 ml) in a round bottom flask under a nitrogen atmosphere and during stirring at 130° C., benzophenone tetracarboxylic dianhydride(BDTA) (3.22 g) dissolved in DMF (50 ml) was added slowly over 1 h to the diamine solution via a dropping funnel. After the BDTA had been added the solution was heated just m boiling point. The solution became cloudy after about 1 h and the solution was left to gently reflux under an air condenser for 6–8 h. The precipitate that formed was filtered washed in ethanol and dried under vacuum over $P_2O_5$ at room temperature; the yield was 75%. The product was cleaned by extracting with ethanol in a soxhlet apparatus. The cleaned product was pale yellow solid which did not melt up to 400° C. Fourier Transform infra-red peaks at 3344, 3221, 1778, 1721, 1682, 713 $cm^{-1}$, and proton nmr peaks at 8.3, 8.1(imide), 6.7, 7.1(aminoaromatic) and 5.1 ($NH_2$) ppm confirmed its structure.

EXAMPLE 3a

Synthesis of 2,6-bis(3-amino(methyldiethyl)phenyl)-benzo [1,2-c:4,5-c']-dipyrrole-1,3,5,7(1H,6H) -tetrone Ethacure (Registered Trade Mark) 100 (Ethyl Corp) (3.31 g) and 1,4-diazabicyclo[2.2.2]octane (1.0 g) were dissolved in dimethylformamide(DMF) (50 ml) in a round bottom flask under a nitrogen atmosphere and during stirring, pyromellitic dianhydride(PMDA) (2.02 g) dissolved in DMF (50 ml) was added slowly over 1 hour to the diamine solution via a dropping funnel. After all the PMDA had been added the solution was heated just to boiling point. The solution became very dark, almost black, after heating, the solution was left to gently reflux under an air condenser overnight (about 16 h). The solution was then concentrated and the concentrate added to a 50/50 methanol/water solution to form a precipitate. The precipitate that formed was filtered off and dried under vacuum over $P_2O_5$ at room temperature; the yield was 82%. The product can be cleaned by washing first with cold sodium bicarbonate solution then with cold ethanol. The cleaned product was orange in colour and had a DSC melting point of 304° C. Fourier Transform infra-red, proton and $C^{13}$ nmr spectroscopy in $CDCl_3$ confirmed its structure. This diaminobisimide was soluble in acetone, chloroform and dichloromethane.

EXAMPLE 3b

The compound above was also prepared in 90% yield by stirring molten Ethacure (Registered Trade Mark) 100 (2 mole) with dry pyromellitic dianhydride at room temperature and then slowly heating the mixture to 160° C. under nitrogen for 2 h.

EXAMPLE 3c

The compound above was prepared in 86% yield by a further variation of the process of this invention in which the powdered salt of pyromellitic acid and Ethacure (Registered Trade Mark) 100 was suspended in water, the suspension degasseal under vacuum then heated with stirring in a sealed vessel at 250° C. and 3585 KPa for 4 hours.

EXAMPLE 4

Synthesis of 5,5'-carbonylbis[2-(3-amino(methyldithiomethyl)phenyl)]-1H-isoindole-1,3(2H) - dione Ethacure (Registered Trade Mark) 300 from Ethyl Corp (an isomeric mixture of methyldithiomethyl-metaphenylenediamines)(7.96 g) and 1,4-diazabicycto [2.2.2]octane (3.0 g) were dissolved in dimethylformamide (DMF) (50 ml) in a round bottom flask under a nitrogen atmosphere and during stirring, benzophenone tetracarboxylic dianhydride(BDTA) (2.02 g) dissolved in DMF (50 ml) was added slowly over 1 hour to the diamine solution via a dropping funnel. After all the BDTA had been added the solution was heated just to boiling point. After heating, the solution had become a clear orange, it was then left to gently reflux under an air condenser for about 4 h. The solution was then concentrated and the concentrate added to methanol to form a precipitate. The precipitate that formed was filtered off and dried under vacuum over $P_2O_5$ at room temperature; the yield was 73%. The product was sand colour and had a melting range of 175°–200° C. Fourier Transform infra-red, proton and $C^{13}$ nmr spectroscopy in $CDCl_3$ confirmed its structure.

EXAMPLE 5

Synthesis of 2,6-bis(4-aminophenyl)-benzo[1,2-c:4,5-c']-dipyrrole-1,3,5,7 (2H,6H)tetrone A mixture of pyromellitic acid (5.59 g; 0.022 mole) and 1,4-phenylenediamine (4.76 g; 0.044 mole) in water was degassed under vacuum and the air in the sealed vessel replaced with nitrogen. The mixture was heated with stirring at 250° C. and 3585 KPa for 4 h. When cool the fine powder was filtered off, washed with water, and dried to give the diaminobisimide 6.66 g (84% yield calculated as monomer). The product had an infra-red spectrum similar to the product prepared in dimethyl formamide using pyromellitic dianhydride.

EXAMPLE 6

Synthesis of 2,6-bis(3-amino-2,4,6-trimethylphenyl)-benzo[12-c:4,5-c']-dipyrrole-1,3,5,7(2H,6H)-tetrone A mixture of pyromellitic acid (5.08 g; 0.02 mole) and 2,4,6-trimethyl-1,3-phenylenediamine (6.00 g; 0.04 mole) in water was degassed under vacuum and the air in the sealed vessel replaced with nitrogen. The mixture was heated with stirring at 250° C. and 3585 KPa for 4 h. When cool the fine powder was filtered off, washed with water, and dried to give the diaminobisimide 7.27 g (70% yield calculated as monomer). The reaction product gave a 1H nmr spectrum in dimethylsulphoxide typical of a bisimide and confirmed the absence of starting materials, oligomers and side reaction products.

EXAMPLE 7

A typical curing resin by melt blending (a) Preparation of the resin

A mixture of Araldite (Registered Trade Mark) MY720 (24.5 g) and Epikote (Registered Trade Mark) 8283 IQ (a DGEBA type epoxy) (19.0 g) was heated on a rotary evaporator at 100° C. under 0.5 mm vacuum for 1 hour. The diaminobisimide hardener CBH-104 (26.7 g) was added and thoroughly mixed and then heated at 145°–155° C./0.5 mm for 30 minutes.

(b) Curing

The neat resin mixture was transferred to heated moulds and cured at 135° C. for 1.5 h, 175° C. for 2 h and then 190° C. for 3 h and finally post cured at 205° C. for 3 h.

EXAMPLES 8–23

Other curable resin formulations

In other examples, the ratio of Araldite (Registered Trade Mark) MY720 to Epikote (Registered Trade Mark) 8283 IQ was varied. Some preparations used CBH-103 instead of CBH-104. Additives such as Ultem (Registered Trade Mark) 1000 and polyethersulfone (prepared according to A Noshay, M Matzner and C. N. Merriam, *J. Polym. Sci:* Part A-1, 9, 3147 (1971)) were dissolved in methylene chloride and added to the epoxy mixture, the methylene chloride removed under vacuum and then the mixture heated at 100° C./0.5 mm for 1 hour. When methyl ethyl ketone was used it was added at the same time as the CBH-103 or CBH-104 and then removed under vacuum. Control examples were cured by heating at 100° C. for 1 h, 140° C. for 1 h and then 180° C. for 4 h. The diaminobisimide compounds CBH-103 and CBH-104 are somewhat less reactive than DDS as shown by the higher peak temperatures for DSC cures listed in Table 1 and therefore benefit from a post cure at temperatures over 200° C. Alternatively, a catalyst may be used.

Table 2 shows that when the polyepoxide is a mixture of MY720 and DGEBA, the formulations of the invention when cured have much higher Tg values than the corresponding prior art composition using DDS as hardener. In addition, the new cured resins have the same or greater toughness which can be further increased with the addition of thermoplastics such as Ultem (Registered Trade Mark) 1000 or polyethersulfones.

EXAMPLES 24 and 25

Preparation of typical laminates (a) Preparation of prepregs

Resins wherein the epoxy component was a 85% MY720/15% DGEBA mixture, containing differing levels of CBH-103 diaminobisimide were dissolved in methyl ethyl ketone and painted on to Fiberite High Performance Structural W322 woven carbon fibre cloth. The prepreg was dried in a stream of warm air for 10 minutes and then "B" staged in an oven at 90° C. for 60 sec. The prepregs had a mean resin content of 38%.

(b) Laminate production

A 20 ply laminate was laid up according to BSS 7273 from each prepreg and cured in an autoclave at 100° C. for 1 h, 140° C. for 1 h and then 180° C. for 4 h under a pressure of 620 kPa. Mode I interlaminar fracture toughness of each 20 ply cloth laminate was tested according to BSS 7273; the values obtained are given in Table 3, which shows that laminates (composites) prepared from the cured resins of the invention have mode I interlaminar fracture toughness values which exceed the minimum value of 175 $Jm^{-2}$ (area) specified in BMS 8-256F.

EXAMPLE 26

Hot/wet resistance of the cured resins and laminates

Water in vapour or liquid form has a deleterious effect on some cured resins, lowering Tg and hence use temperature ceiling or causing delamination and microcracking in aircraft laminates due to expansion and contraction of the wet laminate with changing environmental conditions. The possible effect of water on a cured composite is assessed by the hot water uptake test which involves measuring water uptake after soaking samples in deionized water at 71° C. for up to 37 days. Table 4 shows that the water uptake of the formulations of the invention when cured is less than those cured with DDS. The water uptake of the corresponding composite is less than that of a commercial toughened composite and similar to that of the experimental DDS cured laminate.

TABLE 1

Dynamic DSC cures of Epoxy Resins (at 10° C./min)

| Run | Epoxies | Wt % DGEBA[a] | Curing Agent | Equivalent Ratio | $T_{max}$ (°C.) | $\Delta H$ (kJ/mole) |
|---|---|---|---|---|---|---|
| Control | MY720 | 0 | DDS | 0.5 | 280 | 123 |
| Control | MY720 | 0 | DDS | 0.7 | 274 | 120 |
| Control | MY720 | 0 | DDS | 1.0 | 235 | 111 |
| Control | MY720 | 0 | DDS | 1.2 | 227 | 106 |
| A | MY720 | 0 | CBH-104 | 0.5 | 291 | 115 |
| B | MY720 | 0 | CBH-104 | 1.0 | 274 | 91 |
| C | MY720 | 0 | CBH-104 | 1.2 | 250 | 120 |
| D | MY720/DGEBA | 43.7 | CBH-104 | 0.61 | 297 | 100 |
| E | MY720/DGEBA | 43.7 | CBH-104 | 1.0 | 290 | 109 |
| F | MY720 | 0 | CBH-103 | 0.5 | 282 | 97 |
| G | MY720 | 0 | CBH-103 | 1.0 | 268 | 91 |
| H | MY720 | 0 | CBH-103 | 1.5 | 266 | 89 |
| I | MY720/DGEBA | 24.6 | CBH-103 | 0.61 | 297 | 80 |
| J | MY720/DGEBA | 43.7 | CBH-103 | 1.0 | 308 | 72 |
| K | MY720/DGEBA | 43.7 | CBH-103[b] | 1.0 | 174 | 69 | a Based on total weight of epoxies
b Plus 1.0% of $BF_3.EtNH_2$ catalyst

TABLE 2

Epoxy Resins Cured with Dialkyldiaminobisimides

| Example | Epoxies | Wt % DGEBA[a] | Curing Agent | Equivalent Ratio (curing agent/total epoxy) | Toughening Agent | Wt % | Tg | E' (at 40° C.) (GPa) | $K_q^c$ (MPa $m^{1/2}$) |
|---|---|---|---|---|---|---|---|---|---|
| Control | DGEBA | 100 | DDS | 1.0 | — | — | 211 | 1.4 | — |
| Control | DGEBA | 100 | DDS | 1.2 | — | — | 192 | 1.98 | .63 |
| Control | MY720/DGEBA | 84.8 | DDS | 1.2 | — | — | 190 | 2.13 | .61 |
| Control | MY720/DGEBA | 58.3 | DDS | 1.2 | — | — | 220 | 2.66 | .62 |
| Control | MY720/DGEBA | 58.3 | DDS | 0.90 | — | — | 210 | 2.15 | .58 |
| Control | MY720/DGEBA | 42.9 | DDS | 0.60 | — | — | 216 | 1.56 | .60 |
| Control | MY720/DGEBA | 31.8 | DDS | 0.90 | — | — | 233 | 2.49 | .49 |
| Control | MY720 | 0 | DDS | 0.66 | — | — | 265 | — | .45 |
| 8 | MY720 | 0 | 104 | 0.64 | — | — | — | — | .47 |
| 7 | MY720/DGEBA | 43.7 | 104 | 0.61 | — | — | 222 | 1.62 | .51 |
| 9 | MY720/DGEBA | 43.7 | 104[b] | 0.61 | — | — | 245 | 1.85 | .64 |
| 10 | MY720/DGEBA | 43.7 | 104[b] | 1.0 | — | — | 250 | 1.96 | .74 |
| 11 | MY720/DGEBA | 43.7 | 104 | 0.61 | Ultem 1000 | 5 | 243 | 2.16 | .71 |
| 12 | MY720 | 0 | 1.3 | 0.61 | — | — | 270 | — | .51 |
| 13 | MY720/DGEBA | 24.6 | 103 | 0.61 | — | — | 254 | 2.04 | .65 |
| 14 | MY720/DGEBA | 24.6 | 103 | 0.61 | Ultem 1000 | 10 | 210 | 2.44 | .74 |
| 15 | MY720/DGEBA | 43.7 | 103 | 0.61 | — | — | 246 | 2.31 | .65 |
| 16 | MY720/DGEBA | 43.7 | 103 | 0.61 | Ultem 1000 | 10 | 250 | 2.21 | .64 |
| 17 | MY720/DGEBA | 43.7 | 103 | 0.61 | Ultem 1000 | 15 | 251 | 2.15 | .69 |
| 18 | MY720/DGEBA | 43.7 | 103 | 0.61 | Polysulfone | 10 | | | .62 |
| 19 | MY720/DGEBA | 43.7 | 103 | 0.61 | Polysulfone | 15 | | | .62 |
| 20 | MY720/DGEBA | 43.7 | 103 | 0.61 | Polysulfone | 20 | | | .67 |
| 21 | MY720/DGEBA | 43.7 | 103 | 0.61 | Polysulfone | 25 | | | .73 |
| 22 | MY720/DGEBA | 43.7 | 103[b] | 0.61 | — | — | 264 | 2.29 | .58 |
| 23 | MY720/DGEBA | 43.7 | 103[b] | 1.0 | — | — | 261 | 2.20 | .61 | a Based on total weight of epoxies
b Dissolved in MEK first
c Determined by CSIRO Composite Testing Group

TABLE 3

Mode I Interlaminar Fracture Toughness Values of Some Epoxy Composites

| Example | Composition[a] | Fracture Toughness (J/m²) | | |
|---|---|---|---|---|
| | | Initiation | Arrest | Area |
| Control | Fiberite HMF 322/34 (MY720/DDS/rubber) | 468 | 338 | 389 |
| 24 | MY720 (85%)/DGEBA (15%)/CBH-103 (1.0) | 320 | 256 | 314 |

TABLE 3-continued

Mode I Interlaminar Fracture Toughness Values of Some Epoxy Composites

| | | Fracture Toughness (J/m²) | | |
|---|---|---|---|---|
| Example | Composition[a] | Initiation | Arrest | Area |
| 25 | MY720 (85%)/DGEBA (15%)/CBH-103 (0.6) | 387 | 268 | 343 |

[a]Wt % based on the total weight of the epoxy for the epoxy composition; equivalent ratio of the curing agent to epoxies for the curing agent composition.

TABLE 4

Hot/wet Properties of Resins and Laminates

| | | | Water Uptake % | | |
|---|---|---|---|---|---|
| Example | Form | Composition[a] | 6 days | 13 days | 37 days |
| Control | Resin | MY720 (68%)/DGEBA (32%)/DDS (0.9) | 2.87 | 3.13 | — |
| 15 | Resin | MY720 (56%)/DGEBA (44%)/CBH-103 (0.61) | 1.48 | 1.61 | 1.91 |
| 7 | Resin | MY720 (56%)/DGEBA (44%)/CBH-104 (0.61) | 1.66 | 1.83 | 1.91 |
| 16 | Resin | MY720 (56%)/DGEBA (44%)/CBH-103 (0.61)/Ultem1000 (10%) | 1.68 | 2.17 | 2.97 |
| 24 | Laminate | MY720 (85%)/DGEBA (15%)/CBH-103 (1.0) | 0.85 | 0.85 | — |
| 25 | Laminate | MY720 (85%)/DGEBA (15%)/CBH-103 (0.6) | 0.98 | 1.18 | — |
| Control | Laminate | Fiberite HMF 322/34 (MY720/DDS/rubber) | 1.32 | 1.44 | — |
| Control | Laminate | MY720 (68%)/DGEBA (32%)/DDS (0.9) | 0.97 | 1.07 | — |

[a]Wt % based on the total weight of the epoxy for the epoxy composition; equivalent ratio of the curing agent to epoxies for the curing agent composition.

We claim:

1. A curing agent for use in an epoxy resin formulation, wherein the curing agent is substantially free of oligomers and amide impurities, and comprises a diaminobisimide compound of formula (Ia):

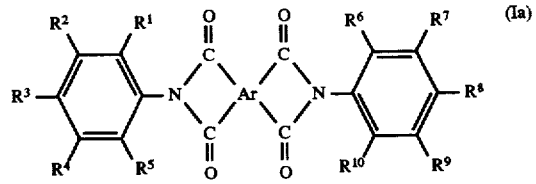

wherein:

$R^1$ to $R^{10}$ are the same or different and each is selected from the group consisting of hydrogen, alkyl, alkylthio, alkoxy, dialkylamino, alkylamino and amino; and Ar is an optionally substituted aromatic residue, with the proviso that at least one of $R^1$ to $R^5$ and $R^6$ to $R^{10}$ is an alkyl group, and at least one of $R^2$ to $R^4$ and $R^7$ to $R^9$ is an amino group, wherein the diaminobisimide compound of formula (Ia) is produced by heating (a) at least about two molar proportions of one or more aromatic diamines selected from the group consisting of

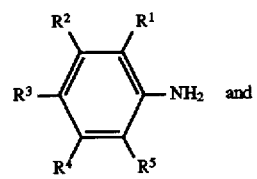

-continued

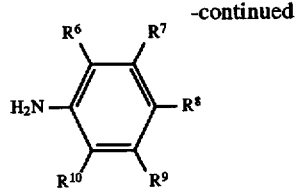

with (b) about 1 molar proportion of an aromatic tetra-carboxylic acid of the formula III, or its corresponding dianhydride, $$(HOOC)_2Ar(COOH)_2 \quad (III)$$

wherein Ar is as defined above.

2. A curing agent as claimed in claim 1 wherein the diaminobisimide compound of formula (Ia) is produced by heating in the presence of a polar solvent.

3. A curing agent as claimed in claim 1 wherein the diaminobisimide compound of formula (Ia) is produced by heating in the presence of about 0.1 to 2 molar proportions of a tertiary amine.

4. A curing agent as claimed in claim 3 wherein the diaminobisimide compound of formula (Ia) is produced by heating in the presence of a polar solvent.

5. A curing agent as claimed in claim 1 wherein at least three of $R^1$, $R^5$, $R^6$ and $R^{10}$ are methyl or sterically larger groups.

6. An epoxy resin formulation comprising a mixture of a curing agent and one or more polyepoxides, wherein the curing agent is a compound of the formula (Ia) as claimed in claim 1.

7. An epoxy resin formulation comprising a mixture of a curing agent and one or more polyepoxides, wherein the curing agent is a compound of the formula (Ia) as claimed in claim 5.

8. A cured epoxy resin wherein the cured epoxy resin is produced by heating the formulation as claimed in claim 6 at a temperature up to about 250° C.

9. An impregnated fibre reinforced material, wherein the fibre reinforcements are coated with an epoxy resin formulation as claimed in claim 6.

10. A material comprising an assembly of reinforcing fibers in a matrix of cured epoxy resin, wherein the cured epoxy resin is as claimed in claim 8.

11. An epoxy resin formulation comprising a mixture of a curing agent and one or more polyepoxides, wherein the curing agent is substantially free of oligomers and amide impurities and comprises a diaminobisimide compound of formula (I):

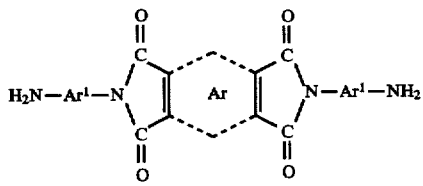

wherein:

Ar$^1$ is an optionally substituted aromatic residue which provides for good conjugation between the nitrogen groups;

Ar is an optionally substituted aromatic residue, wherein the diaminobisimide compound of formula (I) is produced by heating (a) about at least two molar proportions of one or more aromatic diamines selected from the group consisting of

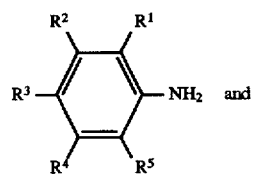

-continued

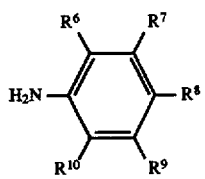

with (b) about 1 molar proportion of an aromatic tetracarboxylic acid of the formula III, or its corresponding dianhydride, $$(HOOC)_2Ar(COOH)_2 \qquad (III)$$

wherein Ar is as defined above, and

R$^1$ to R$^{10}$ are the same or different and each is selected from the group consisting of hydrogen, alkyl, alkylthio, alkoxy, dialkylamino, alkylamino and amino.

12. An epoxy resin formulation as claimed in claim 11 wherein the diaminobisimide compound of formula (I) is produced by heating in the presence of a polar solvent.

13. An epoxy resin formulation as claimed in claim 11 wherein the diaminobisimide compound of formula (I) is produced by heating in the presence of about 0.1 to 2 molar proportions of a tertiary amine.

14. An epoxy resin formulation as claimed in claim 11 wherein in the curing agent at least three of R$^1$, R$^5$, R$^6$ and R$^{10}$ are methyl or sterically larger groups.

15. A cured epoxy resin, characterized in that the cured epoxy resin is produced by heating the formulation as claimed in claim 11 at a temperature up to 250° C.

16. An impregnated fibre reinforced material, characterized in that the fibre reinforcements are coated with an epoxy resin formulation as claimed in claim 11.

17. A material comprising an assembly of reinforcing fibres in a matrix of cured epoxy resin, characterized in that the cured epoxy resin is as claimed in claim 15.

* * * * *